US008920777B2

(12) United States Patent
McTavish

(10) Patent No.: US 8,920,777 B2
(45) Date of Patent: Dec. 30, 2014

(54) TOXINS AND RADIONUCLIDES COUPLED TO IGF-1 RECEPTOR LIGANDS FOR TREATMENT OF CANCER

(75) Inventor: Hugh McTavish, Birchwood, MN (US)

(73) Assignee: IGF Oncology, LLC, Birchwood, MN (US)

( * ) Notice: Subject to any disclaimer, the term of this patent is extended or adjusted under 35 U.S.C. 154(b) by 0 days.

(21) Appl. No.: 13/210,359

(22) Filed: Aug. 15, 2011

(65) Prior Publication Data

US 2011/0301340 A1 Dec. 8, 2011

Related U.S. Application Data

(60) Division of application No. 11/788,627, filed on Apr. 20, 2007, now Pat. No. 8,017,102, which is a continuation-in-part of application No. PCT/US2005/037739, filed on Oct. 21, 2005.

(60) Provisional application No. 60/620,794, filed on Oct. 21, 2004.

(51) Int. Cl.
*A61K 51/00* (2006.01)
*A61M 36/14* (2006.01)
*A61K 47/48* (2006.01)
*A61K 38/30* (2006.01)
*A61K 51/08* (2006.01)

(52) U.S. Cl.
CPC ........... *A61K 38/30* (2013.01); *A61K 47/48238* (2013.01); *A61K 47/48246* (2013.01); *A61K 51/088* (2013.01); *A61K 47/48261* (2013.01)
USPC .......... 424/1.69; 424/1.11; 424/1.65; 514/1.1

(58) Field of Classification Search
CPC ..... A61K 38/00; A61K 38/18; A61K 38/179; A61K 38/177; A61K 38/1764; A61K 38/1709; A61K 38/17; A61K 38/168; A61K 38/164; A61K 38/162; A61K 38/12; A61K 38/16; A61K 38/02; A61K 51/08; A61K 51/088; A61K 2121/00; A61K 2123/00; A61K 47/48261; C07K 14/00; C07K 14/475
USPC ............. 424/1.11, 1.49, 1.65, 1.69, 1.73, 9.1; 530/300; 534/7, 10–16; 514/1, 1.1
See application file for complete search history.

(56) References Cited

U.S. PATENT DOCUMENTS

| | | | | |
|---|---|---|---|---|
| 4,876,242 | A | 10/1989 | Applebaum et al. | |
| 5,122,368 | A | 6/1992 | Greenfield et al. | |
| 7,811,982 | B2 | 10/2010 | McTavish | 424/198.1 |
| 8,017,102 | B2 * | 9/2011 | McTavish | 424/1.69 |
| 2003/0092631 | A1 * | 5/2003 | Deshayes et al. | 514/14 |
| 2003/0138430 | A1 | 7/2003 | Stimmel et al. | |
| 2003/0198598 | A1 | 10/2003 | Albert et al. | |
| 2004/0023887 | A1 | 2/2004 | Pillutla et al. | |
| 2004/0038303 | A1 | 2/2004 | Unger | |
| 2004/0137071 | A1 | 7/2004 | Unger | |
| 2004/0142381 | A1 | 7/2004 | Hubbard et al. | |

FOREIGN PATENT DOCUMENTS

| | | |
|---|---|---|
| WO | WO88/08715 | 11/1988 |
| WO | WO93/21939 | 11/1993 |
| WO | WO98/07864 | 2/1998 |
| WO | WO 01/72771 | * 10/2001 |
| WO | WO0172771 | 10/2001 |
| WO | WO0193900 | 12/2001 |
| WO | WO03/074551 | 9/2003 |
| WO | WO2004/021992 | 3/2004 |

OTHER PUBLICATIONS

Tian et al, Annals of New York Academy of Sciences, 2003, vol. 1002, pp. 165-188.*

Francis et al, Endocrinology, 1989, vol. 124, No. 3, pp. 1173-1183.*

Ayre SG, Garcia y Bellon DP, Garcia DP Jr. 2000. Insulin, chemotherapy, and the mechanisms of malignancy: the design and the demise of cancer, *Medical Hypotheses* 55:330-334.

Abita JP, Gauville C, Balitrand N, Gespach C, Canivet J. 1984. Binding of 125I-insulin to the human histiocytic lymphoma cell line U-937: effect of differentiation with retinoic acid. *Leuk Res.* 8(2):213-21.

Alabaster O, Vonderhaar BK, Shafie SM. 1981. Metabolic modification by insulin enhances methotrexate cytotoxicity in MCF-7 human breast cancer cells. *Eur J Cancer Clin Oncol.* 17(11):1223-8.

Schilsky RL, Bailey BD, Chabner BA. 1981. Characteristics of membrane transport of methotrexate by cultured human breast cancer cells. *Biochem Pharmacol.* 30(12):1537-42.

Oster JB, Creasey WA. 1981. Enhancement of cellular uptake of ellipticine by insulin preincubation. *Eur J Cancer Clin Oncol.* 17(10):1097-103.

Daughaday WH, Rotwein P. 1989. Insulin-like growth factors I and II. Peptide, messenger ribonucleic acid and gene structures, serum, and tissue concentrations. *Endocr Rev.* 10(1):68-91.

Stewart CE, Rotwein P. 1996. Growth, differentiation, and survival: multiple physiological functions for insulin-like growth factors. *Physiol Rev.* Oct. 1996;76(4):1005-26.

Yakar S, Wu Y, Setser J, Rosen CJ. 2002. The role of circulating IGF-I: lessons from human and animal models. *Endocrine.* 19(3):239-48.

Shackney SE, McCormack GW, Cuchural GJ Jr. 1978. Growth rate patterns of solid tumors and their relation to responsiveness to therapy: an analytical review. *Ann. Intern. Med.* 89:107-21.

Poznansky MJ, Singh R, Singh B, Fantus G. 1984. Insulin: carrier potential for enzyme and drug therapy. *Science* 223(4642):1304-6.

Bures L, Bostik J, Motycka K, Spundova M, Rehak L. 1988. The use of protein as a carrier of methotrexate for experimental cancer chemotherapy. III. Human serum albumin-methotrexate derivative, its preparation and basic testing. *Neoplasma* 35:329-42.

Ciftci K, Su J, Trovitch PB. 2003. Growth factors and chemotherapeutic modulation of breast cancer cells. *J Pharm Pharmacol* 55(8):1135-41.

(Continued)

*Primary Examiner* — Dameron Levest Jones
(74) *Attorney, Agent, or Firm* — Hugh McTavish

(57) ABSTRACT

The invention provides an insulin-like growth factor-1 (IGF-1) receptor ligand carrying a therapeutic radionuclide for treatment of cancer is provided. A method of treating cancer using the IGF-1 receptor ligand carrying a therapeutic radionuclide is also provided. An anti-cancer therapeutic agent containing an IGF-1 receptor ligand linked to a toxin is also provided, as are methods of using the toxin conjugates for treatment of cancer.

4 Claims, No Drawings

(56) References Cited

OTHER PUBLICATIONS

Francis GL, Ross M, Ballard FJ, Milner SJ, Senn C, Mcneil KA, Wallace JC, King R, Wells Jr. 1992. Novel recombinant fusion protein analogues of insulin-like growth factor (IGF)-I indicate the relative importance of IGF-binding protein and receptor binding for enhanced biological potency. *J Mol Endocrinol.* 8(3):213-23.

Tomas FM, Knowles SE, Chandler CS, Francis GL, Owens PC, Ballard FJ. 1993. Anabolic effects of insulin-like growth factor-I (IGF-I) and an IGF-I variant in normal female rats. *J Endocrinol.* 137(3):413-21.

Stehle G, Sinn H, Wunder A, Schrenk HH, Schutt S, Maier-Borst W, Heene DL. 1997. The loading rate determines tumor targeting properties of methotrexate-albumin conjugates in rats. *Anticancer Drugs* 8(7):677-85.

Grothey, A. et al., 1999. The role of insulin-like growth factor I and its receptor in cell growth, transformation, apoptosis, and chemoresistance in solid tumors. *J. Cancer Res. Clin. Oncol.* 125:166-173.

Waldow, Stephen M., 1996, Overview of Radiobiology, Chapter 9 in *Introduction to Radiation Therapy,* Charles M. Washington et al. eds.

Satyamarthy, K., et al., 2001, Insulin-like growth factor-1 induces survival and growth of biologically early melanoma cells . . . *Cancer Res.* 61:7318.

Jordan, B.F. et al., 2002, Insulin increases the sensitivity of tumors to irradiation.. Cancer Research 62:3555-3561.

Jordan, B.F. et al., Nitric oxides as a radiosensitizer . . . *Int. J. Cancer* 109:768-773.

Zolzer, F. et al., 2000, Radiation and/or hyperthermia sensitivity of human melanoma cells after several days of incubation in media lacking serum or certain serum components. *Int. J. Radiation Oncology Biol. Phys.* 46:491-497.

Griffin, R.J. et al. 2002. Simultaneous inhibition of the receptor kinase activity of vascular endothelial, fibroblast, and platelet-derived growth factors suppress tumor growth and enhances tumor radiation response. *Cancer Research* 62:1702-1706.

Watanabe, H. et al., 1999, Differential effects of the insulin-like growth factor-1 receptor on radiosensitivity and spontaneous necrosis formation of human glioblastoma cells grown in multicellular spheroids. *Experimental Cell Research* 250:99-111.

Biaglow, J.E., et al., 1979. The enhanced radiation response of in vitro tumor models to insulin. *Int. J. Radiation Oncology Biol. Phys.* 5:1669-1672.

Biaglow, J.E., et al. A metabolic control for the enhancement of radiation response. *Am. J. Roentgenology* 108:405-411.

Bayne, M.L., et al. 1987, Expression of a synthetic gene encoding human insulin-like growth factor I in cultured mouse fibroblasts. *Proc. Natl. Acad. Sci,* 84:2639-2642.

Bayne, M.L., et al. 1988, Structural analogs of human insulin-like growth factor I with reduced affinity for serum binding proteins and the type 2 insulin-like growth factor receptor. *The Journal of Biological Chemistry* 13:6233-6239.

* cited by examiner

SEQUENCE LISTING

```
<160> NUMBER OF SEQ ID NOS: 14

<210> SEQ ID NO 1
<211> LENGTH: 70
```

<212> TYPE: PRT
<213> ORGANISM: Homo sapiens

<400> SEQUENCE: 1

```
Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala
65                  70
```

<210> SEQ ID NO 2
<211> LENGTH: 71
<212> TYPE: PRT
<213> ORGANISM: Artificial
<220> FEATURE:
<223> OTHER INFORMATION: insulin-IGF-1 hybrid

<400> SEQUENCE: 2

```
Phe Val Asn Gln His Leu Cys Gly Ser His Leu Val Glu Ala Leu Tyr
1               5                   10                  15

Leu Val Cys Gly Asp Arg Gly Phe Tyr Phe Asn Lys Pro Thr Gly Tyr
            20                  25                  30

Gly Ser Ser Ser Arg Arg Ala Pro Gln Thr Gly Ile Val Asp Glu Cys
        35                  40                  45

Cys Phe Arg Ser Cys Asp Leu Arg Arg Leu Glu Met Tyr Cys Ala Pro
    50                  55                  60

Leu Lys Pro Ala Lys Ser Ala
65                  70
```

<210> SEQ ID NO 3
<211> LENGTH: 27
<212> TYPE: PRT
<213> ORGANISM: Artificial
<220> FEATURE:
<223> OTHER INFORMATION: peptide ligand

<400> SEQUENCE: 3

```
Ser Phe Tyr Ser Cys Leu Glu Ser Leu Val Asn Gly Pro Ala Glu Lys
1               5                   10                  15

Ser Arg Gly Gln Trp Asp Gly Cys Arg Lys Lys
            20                  25
```

<210> SEQ ID NO 4
<211> LENGTH: 319
<212> TYPE: PRT
<213> ORGANISM: Clostridium perfringens

<400> SEQUENCE: 4

```
Met Leu Ser Asn Asn Leu Asn Pro Met Val Phe Glu Asn Ala Lys Glu
1               5                   10                  15

Val Phe Leu Ile Ser Glu Asp Leu Lys Thr Pro Ile Asn Ile Thr Asn
            20                  25                  30

Ser Asn Ser Asn Leu Ser Asp Gly Leu Tyr Val Ile Asp Lys Gly Asp
        35                  40                  45

Gly Trp Ile Leu Gly Glu Pro Ser Val Val Ser Ser Gln Ile Leu Asn
```

-continued

```
    50                  55                  60

Pro Asn Glu Thr Gly Thr Phe Ser Gln Ser Leu Thr Lys Ser Lys Glu
65                  70                  75                  80

Val Ser Ile Asn Val Asn Phe Ser Val Gly Phe Thr Ser Glu Phe Ile
                85                  90                  95

Gln Ala Ser Val Glu Tyr Gly Phe Gly Ile Thr Ile Gly Glu Gln Asn
            100                 105                 110

Thr Ile Glu Arg Ser Val Ser Thr Thr Ala Gly Pro Asn Glu Tyr Val
        115                 120                 125

Tyr Tyr Lys Val Tyr Ala Thr Tyr Arg Lys Tyr Gln Ala Ile Arg Ile
    130                 135                 140

Ser His Gly Asn Ile Ser Asp Asp Gly Ser Ile Tyr Lys Leu Thr Gly
145                 150                 155                 160

Ile Trp Leu Ser Lys Thr Ser Ala Asp Ser Leu Gly Asn Ile Asp Gln
                165                 170                 175

Gly Ser Leu Ile Glu Thr Gly Glu Arg Cys Val Leu Thr Val Pro Ser
            180                 185                 190

Thr Asp Ile Glu Lys Glu Ile Leu Asp Leu Ala Ala Ala Thr Glu Arg
        195                 200                 205

Leu Asn Leu Thr Asp Ala Leu Asn Ser Asn Pro Ala Gly Asn Leu Tyr
    210                 215                 220

Asp Trp Arg Ser Ser Asn Ser Tyr Pro Trp Thr Gln Lys Leu Asn Leu
225                 230                 235                 240

His Leu Thr Ile Thr Ala Thr Gly Gln Lys Tyr Arg Ile Leu Ala Ser
                245                 250                 255

Lys Ile Val Asp Phe Asn Ile Tyr Ser Asn Asn Phe Asn Asn Leu Val
            260                 265                 270

Lys Leu Glu Gln Ser Leu Gly Asp Gly Val Lys Asp His Tyr Val Asp
        275                 280                 285

Ile Ser Leu Asp Ala Gly Gln Tyr Val Leu Val Met Lys Ala Asn Ser
    290                 295                 300

Ser Tyr Ser Gly Asn Tyr Pro Tyr Ser Ile Leu Phe Gln Lys Phe
305                 310                 315


<210> SEQ ID NO 5
<211> LENGTH: 535
<212> TYPE: PRT
<213> ORGANISM: Corynebacterium diphtheriae
<300> PUBLICATION INFORMATION:
<308> DATABASE ACCESSION NUMBER: P00588
<309> DATABASE ENTRY DATE: 1991-05-01
<313> RELEVANT RESIDUES IN SEQ ID NO: (33)..(567)

<400> SEQUENCE: 5

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95
```

```
Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
            500                 505                 510
```

```
Gly Tyr Gln Lys Thr Val Asp His Thr Lys Val Asn Ser Lys Leu Ser
        515                 520                 525

Leu Phe Phe Glu Ile Lys Ser
    530                 535


<210> SEQ ID NO 6
<211> LENGTH: 462
<212> TYPE: PRT
<213> ORGANISM: Artificial
<220> FEATURE:
<223> OTHER INFORMATION: Fusion of diptheria toxin with IGF-1 variant

<400> SEQUENCE: 6

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335
```

-continued

```
Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe His Ala Phe Val Asn Gln His Leu Cys Gly Ser
385                 390                 395                 400

His Leu Val Glu Ala Leu Tyr Leu Val Cys Gly Asp Arg Gly Phe Tyr
                405                 410                 415

Phe Asn Lys Pro Thr Gly Tyr Gly Ser Ser Ser Arg Arg Ala Pro Gln
            420                 425                 430

Thr Gly Ile Val Asp Glu Cys Cys Phe Arg Ser Cys Asp Leu Arg Arg
        435                 440                 445

Leu Glu Met Tyr Cys Ala Pro Leu Lys Pro Ala Lys Ser Ala
    450                 455                 460


<210> SEQ ID NO 7
<211> LENGTH: 318
<212> TYPE: PRT
<213> ORGANISM: Artificial
<220> FEATURE:
<223> OTHER INFORMATION: Fusion protein of Clostridium perfringens
      enterotoxin with IGF-1 variant

<400> SEQUENCE: 7

Asp Lys Gly Asp Gly Trp Ile Leu Gly Glu Pro Ser Val Val Ser Ser
1               5                   10                  15

Gln Ile Leu Asn Pro Asn Glu Thr Gly Thr Phe Ser Gln Ser Leu Thr
            20                  25                  30

Lys Ser Lys Glu Val Ser Ile Asn Val Asn Phe Ser Val Gly Phe Thr
        35                  40                  45

Ser Glu Phe Ile Gln Ala Ser Val Glu Tyr Gly Phe Gly Ile Thr Ile
    50                  55                  60

Gly Glu Gln Asn Thr Ile Glu Arg Ser Val Ser Thr Thr Ala Gly Pro
65                  70                  75                  80

Asn Glu Tyr Val Tyr Tyr Lys Val Tyr Ala Thr Tyr Arg Lys Tyr Gln
                85                  90                  95

Ala Ile Arg Ile Ser His Gly Asn Ile Ser Asp Asp Gly Ser Ile Tyr
            100                 105                 110

Lys Leu Thr Gly Ile Trp Leu Ser Lys Thr Ser Ala Asp Ser Leu Gly
        115                 120                 125

Asn Ile Asp Gln Gly Ser Leu Ile Glu Thr Gly Glu Arg Cys Val Leu
    130                 135                 140

Thr Val Pro Ser Thr Asp Ile Glu Lys Glu Ile Leu Asp Leu Ala Ala
145                 150                 155                 160

Ala Thr Glu Arg Leu Asn Leu Thr Asp Ala Leu Asn Ser Asn Pro Ala
                165                 170                 175

Gly Asn Leu Tyr Asp Trp Arg Ser Ser Asn Ser Tyr Pro Trp Thr Gln
            180                 185                 190

Lys Leu Asn Leu His Leu Thr Ile Thr Ala Thr Gly Gln Lys Tyr Arg
        195                 200                 205

Ile Leu Ala Ser Lys Ile Val Asp Phe Asn Ile Tyr Ser Asn Asn Phe
    210                 215                 220

Asn Asn Leu Val Lys Leu Glu Gln Ser Leu Gly Asp Gly Val Lys Asp
225                 230                 235                 240
```

His Tyr Val Asp Ile His Ala Phe Val Asn Gln His Leu Cys Gly Ser
245 250 255

His Leu Val Glu Ala Leu Tyr Leu Val Cys Gly Asp Arg Gly Phe Tyr
260 265 270

Phe Asn Lys Pro Thr Gly Tyr Gly Ser Ser Ser Arg Arg Ala Pro Gln
275 280 285

Thr Gly Ile Val Asp Glu Cys Cys Phe Arg Ser Cys Asp Leu Arg Arg
290 295 300

Leu Glu Met Tyr Cys Ala Pro Leu Lys Pro Ala Lys Ser Ala
305 310 315

<210> SEQ ID NO 8
<211> LENGTH: 67
<212> TYPE: PRT
<213> ORGANISM: Homo sapiens

<400> SEQUENCE: 8

Ala Tyr Arg Pro Ser Glu Thr Leu Cys Gly Gly Glu Leu Val Asp Thr
1 5 10 15

Leu Gln Phe Val Cys Gly Asp Arg Gly Phe Tyr Phe Ser Arg Pro Ala
20 25 30

Ser Arg Val Ser Arg Arg Ser Arg Gly Ile Val Glu Glu Cys Cys Phe
35 40 45

Arg Ser Cys Asp Leu Ala Leu Leu Glu Thr Tyr Cys Ala Thr Pro Ala
50 55 60

Lys Ser Glu
65

<210> SEQ ID NO 9
<211> LENGTH: 70
<212> TYPE: PRT
<213> ORGANISM: artificial
<220> FEATURE:
<223> OTHER INFORMATION: human IGF-1 with position 3 changed to Arg

<400> SEQUENCE: 9

Gly Pro Arg Thr Leu Cys Gly Ala Glu Leu Val Asp Ala Leu Gln Phe
1 5 10 15

Val Cys Gly Asp Arg Gly Phe Tyr Phe Asn Lys Pro Thr Gly Tyr Gly
20 25 30

Ser Ser Ser Arg Arg Ala Pro Gln Thr Gly Ile Val Asp Glu Cys Cys
35 40 45

Phe Arg Ser Cys Asp Leu Arg Arg Leu Glu Met Tyr Cys Ala Pro Leu
50 55 60

Lys Pro Ala Lys Ser Ala
65 70

<210> SEQ ID NO 10
<211> LENGTH: 83
<212> TYPE: PRT
<213> ORGANISM: Artificial
<220> FEATURE:
<223> OTHER INFORMATION: variant IGF-1 with reduced binding to the soluble IGF-1 binding proteins

<400> SEQUENCE: 10

Met Phe Pro Ala Met Pro Leu Ser Ser Leu Phe Val Asn Gly Pro Arg
1 5 10 15

Thr Leu Cys Gly Ala Glu Leu Val Asp Ala Leu Gln Phe Val Cys Gly

```
            20                  25                  30

Asp Arg Gly Phe Tyr Phe Asn Lys Pro Thr Gly Tyr Gly Ser Ser Ser
        35                  40                  45

Arg Arg Ala Pro Gln Thr Gly Ile Val Asp Glu Cys Cys Phe Arg Ser
    50                  55                  60

Cys Asp Leu Arg Arg Leu Glu Met Tyr Cys Ala Pro Leu Lys Pro Ala
65                  70                  75                  80

Lys Ser Ala


<210> SEQ ID NO 11
<211> LENGTH: 275
<212> TYPE: PRT
<213> ORGANISM: Artificial
<220> FEATURE:
<223> OTHER INFORMATION: CPE residues 45-223 fused to long-R3-IGF-1

<400> SEQUENCE: 11

Met His His His His His His Gly Asp Asp Asp Asp Lys Asp Lys Gly
1               5                   10                  15

Asp Gly Trp Ile Leu Gly Glu Pro Ser Val Val Ser Ser Gln Ile Leu
            20                  25                  30

Asn Pro Asn Glu Thr Gly Thr Phe Ser Gln Ser Leu Thr Lys Ser Lys
        35                  40                  45

Glu Val Ser Ile Asn Val Asn Phe Ser Val Gly Phe Thr Ser Glu Phe
    50                  55                  60

Ile Gln Ala Ser Val Glu Tyr Gly Phe Gly Ile Thr Ile Gly Glu Gln
65                  70                  75                  80

Asn Thr Ile Glu Arg Ser Val Ser Thr Thr Ala Gly Pro Asn Glu Tyr
                85                  90                  95

Val Tyr Tyr Lys Val Tyr Ala Thr Tyr Arg Lys Tyr Gln Ala Ile Arg
            100                 105                 110

Ile Ser His Gly Asn Ile Ser Asp Asp Gly Ser Ile Tyr Lys Leu Thr
        115                 120                 125

Gly Ile Trp Leu Ser Lys Thr Ser Ala Asp Ser Leu Gly Asn Ile Asp
    130                 135                 140

Gln Gly Ser Leu Ile Glu Thr Gly Glu Arg Cys Val Leu Thr Val Pro
145                 150                 155                 160

Ser Thr Asp Ile Glu Lys Glu Ile Leu Asp Leu Ala Ala Ala Thr Glu
                165                 170                 175

Arg Leu Asn Leu Thr Asp Ala Leu Asn Ser Asn Pro Ala Gly Asn Leu
            180                 185                 190

Met Phe Pro Ala Met Pro Leu Ser Ser Leu Phe Val Asn Gly Pro Arg
        195                 200                 205

Thr Leu Cys Gly Ala Glu Leu Val Asp Ala Leu Gln Phe Val Cys Gly
    210                 215                 220

Asp Arg Gly Phe Tyr Phe Asn Lys Pro Thr Gly Tyr Gly Ser Ser Ser
225                 230                 235                 240

Arg Arg Ala Pro Gln Thr Gly Ile Val Asp Glu Cys Cys Phe Arg Ser
                245                 250                 255

Cys Asp Leu Arg Arg Leu Glu Met Tyr Cys Ala Pro Leu Lys Pro Ala
            260                 265                 270

Lys Ser Ala
        275


<210> SEQ ID NO 12
```

-continued

```
<211> LENGTH: 472
<212> TYPE: PRT
<213> ORGANISM: Artificial
<220> FEATURE:
<223> OTHER INFORMATION: Fusion protein containing residues 1-389 of
      diphtheria toxin followed by long-R3-IGF-1

<400> SEQUENCE: 12

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
```

-continued

```
    370                 375                 380

His Lys Thr His Ala Met Phe Pro Ala Met Pro Leu Ser Ser Leu Phe
385                 390                 395                 400

Val Asn Gly Pro Arg Thr Leu Cys Gly Ala Glu Leu Val Asp Ala Leu
                405                 410                 415

Gln Phe Val Cys Gly Asp Arg Gly Phe Tyr Phe Asn Lys Pro Thr Gly
            420                 425                 430

Tyr Gly Ser Ser Ser Arg Arg Ala Pro Gln Thr Gly Ile Val Asp Glu
        435                 440                 445

Cys Cys Phe Arg Ser Cys Asp Leu Arg Arg Leu Glu Met Tyr Cys Ala
    450                 455                 460

Pro Leu Lys Pro Ala Lys Ser Ala
465                 470


<210> SEQ ID NO 13
<211> LENGTH: 6084
<212> TYPE: DNA
<213> ORGANISM: Artificial
<220> FEATURE:
<223> OTHER INFORMATION: Plasmid for expression of CPE-IGF-1 fusion
      protein

<400> SEQUENCE: 13

tggcgaatgg gacgcgccct gtagcggcgc attaagcgcg gcgggtgtgg tggttacgcg     60

cagcgtgacc gctacacttg ccagcgccct agcgcccgct cctttcgctt tcttcccttc    120

ctttctcgcc acgttcgccg gctttccccg tcaagctcta aatcgggggc tccctttagg    180

gttccgattt agtgctttac ggcacctcga ccccaaaaaa cttgattagg gtgatggttc    240

acgtagtggg ccatcgccct gatagacggt ttttcgccct ttgacgttgg agtccacgtt    300

ctttaatagt ggactcttgt tccaaactgg aacaacactc aaccctatct cggtctattc    360

ttttgattta taagggattt tgccgatttc ggcctattgg ttaaaaaatg agctgattta    420

acaaaaattt aacgcgaatt ttaacaaaat attaacgttt acaatttcag gtggcacttt    480

tcggggaaat gtgcgcggaa cccctatttg tttatttttc taaatacatt caaatatgta    540

tccgctcatg aattaattct tagaaaaact catcgagcat caaatgaaac tgcaatttat    600

tcatatcagg attatcaata ccatattttt gaaaaagccg tttctgtaat gaaggagaaa    660

actcaccgag gcagttccat aggatggcaa gatcctggta tcggtctgcg attccgactc    720

gtccaacatc aatacaacct attaatttcc cctcgtcaaa aataaggtta tcaagtgaga    780

aatcaccatg agtgacgact gaatccggtg agaatggcaa aagtttatgc atttctttcc    840

agacttgttc aacaggccag ccattacgct cgtcatcaaa atcactcgca tcaaccaaac    900

cgttattcat tcgtgattgc gcctgagcga gacgaaatac gcgatcgctg ttaaaaggac    960

aattacaaac aggaatcgaa tgcaaccggc gcaggaacac tgccagcgca tcaacaatat   1020

tttcacctga atcaggatat tcttctaata cctggaatgc tgttttcccg gggatcgcag   1080

tggtgagtaa ccatgcatca tcaggagtac ggataaaatg cttgatggtc ggaagaggca   1140

taaattccgt cagccagttt agtctgacca tctcatctgt aacatcattg gcaacgctac   1200

ctttgccatg tttcagaaac aactctggcg catcgggctt cccatacaat cgatagattg   1260

tcgcacctga ttgcccgaca ttatcgcgag cccatttata cccatataaa tcagcatcca   1320

tgttggaatt taatcgcggc ctagagcaag acgtttcccg ttgaatatgg ctcataacac   1380

cccttgtatt actgtttatg taagcagaca gttttattgt tcatgaccaa aatcccttaa   1440
```

```
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatgtcc gcaccaacgc gcagcccgga ctcggtaatg gcgcgcattg   3840
```

```
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatcga tctcgatccc   4980
gcgaaattaa tacgactcac tataggggaa ttgtgagcgg ataacaattc ccctctagaa   5040
ataattttgt ttaactttaa gaaggagata tacatatgca ccatcaccat caccatggtg   5100
acgatgacga taaggataaa ggcgatggtt ggatcctggg cgaaccgtca gtggtttcaa   5160
gccagattct gaacccgaac gaaacgggta cctttagcca atcactgacc aaatctaaag   5220
aagtatctat caacgtgaac ttttcagttg gttttacctc tgaattcatc caagcatctg   5280
tggaatatgg ctttggcatc accatcggcg aacagaatac catcgaacgc tctgtatcta   5340
caactgctgg tccaaatgaa tatgtgtatt acaaggtgta tgcgacctat cgcaagtatc   5400
aggcgatccg gatttcccat ggtaatatct ctgatgatgg ctccatttat aaactgaccg   5460
gcatttggct gagcaaaaca tctgcggata gcttgggcaa tattgatcag ggttcactga   5520
tcgaaaccgg tgaacgctgc gttctgaccg ttccgtctac cgatatcgaa aaagaaatcc   5580
tggatctggc tgctgcgacc gaacgtctga atctgactga tgcactgaac tcaaatcccg   5640
ctggtaatct gatgttccca gccatgccct tgtccagcct gtttgttaac ggcccgcgta   5700
ccctgtgcgg tgctgaactg gttgacgctc tgcagttcgt ttgcggcgac cgtggcttct   5760
acttcaacaa accgactggc tacggctctt cttctcgtcg tgctccgcag actggcatcg   5820
tcgacgaatg ctgcttccgt tcttgcgacc tgcgtcgtct ggaaatgtac tgcgctccgc   5880
tgaaacctgc taaatctgct taatagaagc ttgcggccgc actcgagcac caccaccacc   5940
accactgaga tccggctgct aacaaagccc gaaaggaagc tgagttggct gctgccaccg   6000
ctgagcaata actagcataa ccccttgggg cctctaaacg ggtcttgagg ggttttttgc   6060
tgaaaggagg aactatatcc ggat                                          6084
```

<210> SEQ ID NO 14

-continued

<211> LENGTH: 6673
<212> TYPE: DNA
<213> ORGANISM: Artificial
<220> FEATURE:
<223> OTHER INFORMATION: Plasmid expressing DPT-IGF-1 fusion protein

<400> SEQUENCE: 14

```
tggcgaatgg gacgcgccct gtagcggcgc attaagcgcg gcgggtgtgg tggttacgcg     60
cagcgtgacc gctacacttg ccagcgccct agcgcccgct cctttcgctt tcttcccttc    120
ctttctcgcc acgttcgccg gctttccccg tcaagctcta aatcgggggc tccctttagg    180
gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta taagggattt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
```

-continued

```
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatgtcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
```

-continued

```
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatcga tctcgatccc   4980
gcgaaattaa tacgactcac tataggggaa ttgtgagcgg ataacaattc ccctctagaa   5040
ataattttgt ttaactttaa gaaggagata tacatatggg cgctgatgat gttgttgatt   5100
cttctaaatc ttttgtgatg gaaaactttt cttcgtacca cgggactaaa cctggttatg   5160
tagattccat tcaaaaaggt atacaaaagc caaaatctgg tacacaagga aattatgacg   5220
atgattggaa agggttttat agtaccgaca ataaatacga cgctgcggga tactctgtag   5280
ataatgaaaa cccgctctct ggaaaagctg gaggcgtggt caaagtgacg tatccaggac   5340
tgacgaaggt tctcgcacta aaagtggata atgccgaaac tattaagaaa gagttaggtt   5400
taagtctcac tgaaccgttg atggagcaag tcggaacgga agagtttatc aaaaggttcg   5460
gtgatggtgc ttcgcgtgta gtgctcagcc ttcccttcgc tgaggggagt tctagcgttg   5520
aatatattaa taactgggaa caggcgaaag cgttaagcgt agaacttgag attaattttg   5580
aaacccgtgg aaaacgtggc caagatgcga tgtatgagta tatggctcaa gcctgtgcag   5640
gaaatcgtgt caggcgatca gtaggtagct cattgtcatg catcaacctg gattgggatg   5700
ttatccgtga taaaactaaa actaagatcg aatctctgaa agaacacggt ccgatcaaaa   5760
acaaaatgag cgaaagcccg aacaaaactg tatctgaaga aaaagctaaa cagtacctgg   5820
aagaattcca ccagactgca ctggaacacc cggaactgtc tgaacttaag accgttactg   5880
gtaccaaccc ggtattcgct ggtgctaact acgctgcttg ggcagtaaac gttgctcagg   5940
ttatcgatag cgaaactgct gataacctgg aaaaaactac cgcggctctg tctatcctgc   6000
cgggtatcgg tagcgtaatg ggcatcgcag acggcgccgt tcaccacaac actgaagaaa   6060
tcgttgcaca gtctatcgct ctgagctctc tgatggttgc tcaggccatc ccgctggtag   6120
gtgaactggt tgatatcggt ttcgctgcat acaacttcgt tgaaagcatc atcaacctgt   6180
tccaggttgt tcacaactct tacaaccgcc cggcttactc tccgggtcac aagacgcatg   6240
caatgttccc agccatgccc ttgtccagcc tatttgttaa cggcccgcgt accctgtgcg   6300
gtgctgaact ggttgacgct ctgcagttcg tttgcggtga ccgtggcttc tacttcaaca   6360
aaccgaccgg ttacggttct tcttctcgtc gtgctccgca gaccggtatc gttgacgaat   6420
gctgcttccg ttcttgcgac ctgcgtcgtc tggaaatgta ctgcgctccg ctgaaaccgg   6480
ctaaatctgc ttgatgatgc agcggccgca ctcgagcacc accaccacca ccactgagat   6540
ccggctgcta acaaagcccg aaaggaagct gagttggctg ctgccaccgc tgagcaataa   6600
ctagcataac cccttggggc ctctaaacgg gtcttgaggg gttttttgct gaaaggagga   6660
actatatccg gat                                                      6673
```

TOXINS AND RADIONUCLIDES COUPLED TO IGF-1 RECEPTOR LIGANDS FOR TREATMENT OF CANCER

This application is a divisional application under 35 U.S.C. §120 of U.S. patent application Ser. No. 11/788,627, filed Apr. 20, 2007 now U.S. Pat. No. 8,017,102, which is a continuation-in-part application claiming priority under 35 U.S.C. §120 from international patent application no. PCT/US05,037739, filed Oct. 21, 2005, which claims priority from U.S. provisional patent application Ser. No. 60/620,794, filed Oct. 21, 2004.

BACKGROUND

Currently 1.3 million people are diagnosed with cancer each year in the United States alone, and over 500,000 die. One method emerging as a new type of treatment for cancer is a type of radiation therapy using an antibody coupled to a therapeutic radionuclide, where the antibody recognizes a target that is specific for a particular type of cancer or found predominantly on cancerous cells. Two examples are currently approved for treatment in the United States: ibitrumomab tiuxetan (ZEVALIN®) and tositumomab (BEXAR®). Ibitrumomab tiuxetan recognizes the CD20 antigen, which is found on normal and malignant B cells. The antibody is coupled to a therapeutic Yttrium-90 radionuclide by a tiuxetan chelator moiety. Tositumomab also recognizes the CD20 antigen, but it is labelled with a I-131 radionuclide. Both are used to treat B-cell non-Hodgkin's lymphoma.

Anti-cancer agents involving toxins, such as diphtheria toxin or Pseudomonas exotoxin, coupled to antibodies that recognize targets found on cancerous cells have also been studied, although no agents of this type are currently approved in the United States.

New agents for treating cancer are needed. Preferably the agents would be targeted to cancer cells and largely spare healthy cells.

SUMMARY

The invention provides new anti-cancer therapeutic agents involving ligands to the insulin-like growth factor-1 (IGF-1) receptor, such as IGF-1 itself, coupled to a therapeutic radionuclide or to a cellular toxin such as diphtheria toxin or Pseudomonas exotoxin.

In previous work, toxins and radionuclides have been coupled to antibodies to deliver them to antigens found specifically on cancer cells. One drawback to the use of antibodies is that antibodies are large molecules that often generate an immune response and hypersensitivity response in patients to whom they are administered. This can interfere with their use therapeutically. The size of antibodies also means they may not penetrate solid tumors efficiently. Antibodies also are not typically internalized by the cells to which they bind. They simply sit on the cell surface. With radionuclide-labelled antibodies, it would be somewhat preferable if the radionuclide were internalized to the target cell and thus were closer to the nucleic acids of the cell, which are the therapeutic target of the radioactivity than it is on the surface of the cell. With toxin-conjugated antibodies, it is a larger problem if the antibody and toxin are not internalized into the target cancer cell, since toxins typically must be internalized by the cell in order to kill the cell.

The defining feature of cancer is that cancerous cells divide without appropriate control. Radiation is used in anti-cancer therapy because radiation is more toxic to actively dividing cells than to resting cells that are not dividing. But cancer cells are not always dividing. The effectiveness of radiation therapy could be increased if the cells could be induced to divide at or around the time they are exposed to radiation.

The IGF-1 receptor is significantly overexpressed in most tumors from almost all types of cancer. IGF-1 is a peptide of 70 amino acid residues having 40% identity with proinsulin. (Daughaday, W. H., et al., 1989, *Endocrine Revs.* 10:68.) IGF-1 is secreted by the liver into the circulatory system and stimulates growth of many cell types. IGF-1 is also produced by many cell types throughout the body, including many cancers, for autocrine and paracrine effects. IGF-1 production is stimulated by growth hormone. (Stewart, C. H., e t al., 1996, *Physiol. Revs.* 76:1005; Yakar, S., et al., 2002, *Endocrine* 19:239.) IGF-1 receptors were found to be 43 times more numerous on malignant breast cancer tissue than benign breast tissue (Jammes, H. et al. *Br. J. Cancer* 66:248-253).

IGF-1's biological role is to stimulate cell division. This is significant since radiation is more toxic to dividing cells than non-dividing cells. Thus, a radioactively labelled IGF-1 receptor agonist not only will be targeted with a high degree of specificity to cancer cells, but it may also cause the cells to divide as they are being irradiated, thus sensitizing them to the radiation.

Furthermore, upon binding to its receptor, IGF-1 is internalized to the cell by receptor-mediated endocytosis. This brings a radionuclide attached to IGF-1 or to another IGF-1 receptor ligand into the cell and closer to the target nucleic acids. This factor is more important for toxin-IGF-1 receptor ligand conjugates, since it brings the toxin into the cell, and most toxins must penetrate the cell in order to exert their toxicity.

Accordingly, one embodiment of the invention provides an insulin-like growth factor (IGF-1) receptor ligand carrying a therapeutic radionuclide.

Another embodiment of the invention provides an anti-cancer therapeutic agent comprising: an IGF-1 receptor ligand linked to a toxin.

Another embodiment of the invention provides a method of treating cancer in a mammal involving administering to the mammal a therapeutically effective amount of an IGF-1 receptor ligand carrying a therapeutic radionuclide.

Another embodiment of the invention provides a method of treating cancer in a mammal involving administering to the mammal a therapeutically effective amount of a therapeutic agent containing an IGF-1 receptor ligand linked to a toxin.

Another embodiment of the invention provides a method of inhibiting growth of cancer cells involving contacting the cancer cells with an IGF-1 receptor ligand carrying a therapeutic radionuclide.

Another embodiment of the invention provides a method of inhibiting growth of cancer cells involving contacting the cancer cells with a therapeutic agent containing an insulin-like growth factor-1 (IGF-1) receptor ligand linked to a toxin.

Another embodiment of the invention provides a method of screening a compound for anti-cancer activity involving contacting cancer cells with a compound comprising an IGF-1 receptor ligand carrying a therapeutic radionuclide.

Another embodiment of the invention provides a method of screening a compound for anti-cancer activity involving contacting cancer cells with a compound comprising an IGF-1 receptor ligand linked to a toxin.

DETAILED DESCRIPTION

Definitions

As used herein, the term "toxin" refers to a molecule or moiety that is generally lethal to all cells. This contrasts with traditional anti-cancer chemotherapy agents, which are selectively lethal to dividing cells and less lethal to non-dividing cells. Anti-cancer chemotherapy agents
that are selectively lethal to dividing cells and can be administered sytemically to treat cancer in mammals are excluded from the term "toxin" as used herein.

As used herein, the term "therapeutic radionuclide" refers to an atom that emits a form of radiation that is therapeutically useful to kill cancer cells.

As used herein, the term "containing" is open-ended, allowing the inclusion of other unnamed elements, and has the same meaning as "comprising."

Description

One embodiment of the invention provides an IGF-1 receptor ligand carrying a therapeutic radionuclide. The radionuclide can be directly coupled to the ligand in some embodiments—for example by iodination of tyrosine or histidine residues on a protein ligand with I-131.

In other embodiments, the radionuclide is coupled to the ligand by a linker moiety. The linker moiety may include a chelator for holding the radionuclide. An example of a chelator is tiuxetan [N-[2-bis(carboxymethyl)amino]-(p-isothiocyanateophenyl)-propyl]-[N-[2-bis(carboxymethyl)amino]-2-(methyl)-ethyl]glycine]. Another example of a ligand for coupling is diethelyenetriaminepentaacetic acid (DTPA). Methods of radiolabelling IGF-1 ligands directly or with chelator linkers are described in greater detail in Example 1.

Examples of suitable radionuclides are Iodine-131, Yttrium-90, Indium-111, Rhenium-186, and Lutetium-177. These are all beta or gamma emitters with short half lives. With IGF-1 receptor ligands that are internalized into the cell, alpha emitters may also be therapeutically effective radionuclides. Alpha particles are absorbed in such short distances that they are ordinarily not therapeutically useful when emitted from the surface of a cancer cell or the outer surface of a tumor. But many ligands to IGF-1 receptor will be internalized by receptor-mediated endocytosis. This will bring the radionuclide into the nucleus of the cell, in direct contact with the DNA target. Thus, in that case an alpha emitting radioisotope may be useful.

The IGF-1 receptor ligand carrying a therapeutic radionuclide can be an IGF-1 receptor agonist. An agonist will stimulate cell division, and since radiation is more lethal for dividing cells than non-dividing cells, this will sensitize the cancerous cells to killing by the radiation. An example of a suitable IGF-1 receptor ligand that is an agonist is IGF-1 itself. The sequence of human IGF-1 is presented as SEQ ID NO:1.

Other examples of IGF receptor agonists suitable for use in the invention include variants of IGF-1 that activate the receptor but have reduced affinity for the soluble IGF-1 binding proteins. Some examples are disclosed in U.S. Pat. No. 4,876,242. IGF-1 binding proteins are natural serum proteins that bind to IGF-1, holding it in circulation and extending its biological half-life. It may be advantageous for radiolabelled and toxin-linked IGF-1 receptor ligands of this invention to have reduced binding to the IGF-1 binding proteins, because that reduced binding would accelerate the release of the agent to bind to the IGF-1 receptors. A particularly important variant of IGF-1 that binds to the IGF receptor but not to the soluble IGF binding proteins is the variant in which the first 16 residues of IGF-1 are replaced by the first 17 residues of the B-chain of insulin (U.S. Pat. No. 4,876,242) (SEQ ID NO:2). Another preferred IGF-1 protein variant with reduced binding affinity for the soluble IGF-1 binding proteins is R3-IGF-1 (SEQ ID NO:9), in which the Glu at position 3 of SEQ ID NO:1 is replaced with Arg. Another preferred variant IGF-1 protein is SEQ ID NO:10 (Francis, G. L. et al., 1992, J. Mol. Endocrinol. 8:213-223; Tomas, F. M. et al., 1993, J. Endocrinol. 137:413-421).

The variant IGF-1 protein, preferably includes a polypeptide segment at least 80%, more preferably at least 90% identical to native IGF-1 (SEQ ID NO:1).

In another particular embodiment, the IGF-1 receptor agonist is IGF-2 (SEQ ID NO:8).

In particular embodiments of the invention, the toxin conjugates and radiolabelled agents include a variant IGF-1 protein that has reduced binding affinity for the soluble IGF-1 binding proteins. In particular embodiments, the variant has greater than 100-fold lower, more preferably greater than 1000-fold lower, binding affinity for the soluble IGF-1 binding proteins than does native IGF-1. Binding affinity for the soluble IGF-1 binding proteins can be assayed as described in Bayne, M. L. et al., 1988, *J. Biol. Chem.* 263:6233-6239; and Bayne, M. L. et al., 1987, *Proc. Natl. Acad. Sci. USA* 84:2638-2642. The technique involves measuring the variant IGF-1's inhibition constant for inhibiting $^{125}$I-IGF-1 binding to the acid-stable protein fraction of human serum.

In particular embodiments of the invention, the IGF-1 receptor ligand that is radiolabelled or part of a toxin conjugate has a $K_D$ for the IGF-1 receptor of less than less than 10 μM, less than 1 μM, less than 100 nM, less than 50 nM, less than 20 nM, less than 10 nM, less than 5 nM, less than 2 nM, or less than 1 nM. Preferably, the ligands have a $K_D$ for the IGF-1 receptor of less than about 50 nM, more preferably less than about 20 nM. Binding affinity for the IGF-1 receptor can be determined as described, for instance, in Bayne, M. L. et al., 1988, *J. Biol. Chem.* 263:6233-6239; and Bayne, M. L. et al., 1987, *Proc. Natl. Acad. Sci. USA* 84:2638-2642, by measuring competition with radiolabelled IGF-1 for binding to placental membranes.

In some embodiments, the IGF-1 receptor ligand is an IGF-1 receptor antagonist. Some antagonist peptides are disclosed in U.S. published patent application No. 2004/0023887, including the peptide SFSCLESLVNGPAEKSRGQWDGCRKK (SEQ ID NO:3).

In particular embodiments, the IGF-1 receptor ligand has a greater affinity for the IGF-1 receptor than for the insulin receptor. In particular embodiments, the IGF-1 receptor ligand is not insulin. In particular embodiments, the IGF-1 receptor ligand has a higher affinity for the IGF-1 receptor than for the insulin receptor.

In particular embodiments, the IGF-1 receptor ligand is not an antibody or an antibody fragment. In other embodiments, the IGF-1 receptor ligand is an antibody or antibody fragment.

In particular embodiments, the IGF-1 receptor ligand is a polypeptide of fewer than 200 amino acid residues or fewer than 100 amino acid residues.

One embodiment of the invention is an anti-cancer therapeutic agent containing an IGF-1 receptor ligand linked to a toxin.

In particular embodiments of the toxin conjugates, the IGF-1 receptor ligand is an IGF-1 receptor agonist. For instance, it can be IGF-1 or one of the variant IGF-1s of U.S. Pat. No. 4,876,242 that has reduced binding to the soluble IGF-1 binding proteins.

In some embodiments, the IGF-1 receptor ligand is an IGF-1 receptor antagonist. Some antagonist peptides are disclosed in U.S. published patent application No. 2004/0023887, including the peptide SFSCLESLVNGPAEKSRGQWDGCRKK (SEQ ID NO:3).

In particular embodiments of the toxin conjugates, the IGF-1 receptor ligand has a greater affinity for the IGF-1 receptor than for the insulin receptor. In particular embodiments, the IGF-1 receptor ligand is not insulin. In particular embodiments, the IGF-1 receptor ligand has a higher affinity for the IGF-1 receptor than for the insulin receptor.

In particular embodiments of the toxin conjugates, the IGF-1 receptor ligand is not an antibody or an antibody fragment. In other embodiments, the IGF-1 receptor ligand is an antibody or antibody fragment.

In particular embodiments of the toxin conjugates, the IGF-1 receptor ligand is a polypeptide of fewer than 200 amino acid residues or fewer than 100 amino acid residues.

In particular embodiments, the toxin is diphtheria toxin, Pseudomonas exotoxin, *Clostridium perfringens* enterotoxin, ricin, or a toxic fragment thereof.

In particular embodiments, the toxin portion of the IGF-1 receptor ligand-toxin conjugate is a toxic fragment of a naturally occurring toxin. Most bacterial toxins, such as diphtheria toxin, Pseudomonas exotoxin, and *Clostridium perfringens* enterotoxin, include a receptor-binding moiety that targets the toxin to a particular cell-surface receptor, and a moiety that is responsible for the toxicity of the toxin protein. For instance, *Clostridium perfringens* enterotoxin binds to claudin-3 and claudin-4 on the cell surface. *Clostridium perfringens* enterotoxin (CPE) is a protein of 319 amino acid residues (SEQ ID NO:4). A peptide consisting of residues 290-319 of *Clostridium perfringens* enterotoxin binds to claudin-3 and claudin-4 but is not toxic (Hanna, P. C., et al., 1991, *J. Biol. Chem.* 266:11037-43). Approximately residues 45-116 of CPE are responsible for cytolysis of cells through forming large complexes in the cell membrane (Kokai-Kun, J. F. et al., 1996, *Infect. Immun.* 64:1020-25; Kokai-Kun, J. F. et al., 1997, *Clin. Infect. Dis.* 25 (Suppl. 2):S165-5167; Kokai-Kun, J. F. et al., Infect. Immun. 65:1014-1022; Kokai-Kun, J. F. et al., 1999, *Infect. Immun.* 67:5634-5641; Hanna, P. C., et al., 1991, *J. Biol. Chem.* 266:11037-43). Deletion of just residues 315-319 is enough to abolish binding to the receptors (Kokai-Kun, J. F. et al., 1999, *Infect. Immun.* 67:5634-5641). Thus, in some embodiments of the present toxin conjugates, the toxin moiety of the conjugates is a fragment of CPE containing residues 45-116 of SEQ ID NO:4, but lacking residues 315-319 of SEQ ID NO:4. For instance, the toxin may be residues 1-314, 1-289, 1-116, 45-314, 45-289, 45-116, or 45-223 of SEQ ID NO:4.

In other embodiments, the toxin is diphtheria toxin or a toxic fragment thereof. Diphtheria toxin is a protein of 535 amino acid residues (SEQ ID NO:5). It contains three domains. Residues 1-193 are the catalytic domain, having the ADP-ribosyl transferase activity that is responsible for inactivating elongation factor-2 in cells to kill them (Choe, S. et al., 1992, *Nature* 357:216-222). Approximately residues 203-378 are responsible for translocation of the toxin across the cell membrane (id). And approximately residues 386-535 are responsible for binding to the receptor (id). Fusions of interleukin-2 to residues 1-389 of diphtheria toxin have been found to be more cytotoxic against cells having interleukin-2 receptors than fusions to longer fragments of diphtheria toxin (Williams, D. P. et al., 1990, *J. Biol. Chem.* 265:11885-89); Kiyokawa, T. et al., 1991, *Protein Engineering* 4:463-468). Thus, in a particular embodiment, the toxin portion of the present conjugates is residues 1-389 of SEQ ID NO:5.

In one embodiment, the toxin-IGF-1 receptor ligand conjugate is or comprises SEQ ID NO:6, which is residues 1-389 of diphtheria toxin coupled to the variant IGF-1 SEQ ID NO:2 that does not bind to the soluble IGF-binding proteins. The diphtheria toxin portion (DPT) and IGF-1 portion of the conjugate in SEQ ID NO:6 are separated by a His-Ala linker. In another embodiment, the toxin-IGF-1 receptor ligand conjugate is a DPT-IGF-1 fusion protein that is or comprises SEQ ID NO:12.

In another embodiment, the toxin-IGF-1 receptor ligand conjugate is or comprises SEQ ID NO:7, which is residues 45-289 of *Clostridium perfingens* enterotoxin (CPE) coupled to SEQ ID NO:2. The CPE portion and IGF-1 portion of the conjugate in SEQ ID NO:7 are separated by a His-Ala linker.

In another embodiment, the toxin portion toxin-IGF-1 receptor ligand conjugate is or comprises residues 45-116, 45-223, or 45-310 of SEQ ID NO:4.

In another embodiment, the toxin-IGF-1 receptor ligand conjugate is a CPE-IGF-1 fusion protein that is or comprises SEQ ID NO:11 or residues 14-275 of SEQ ID NO:11. Residues 14-275 of SEQ ID NO:11 are residues 14-223 of CPE at the N-terminus followed by at its C-terminus an IGF-1 variant (SEQ ID NO:10) with reduced binding to the soluble IGF-1 binding proteins.

Toxins can be chemically conjugated to proteinaceous IGF-1 receptor ligands by methods disclosed in U.S. provisional patent application Ser. No. 60/513,048 and international patent application WO2005/041865, which are incorporated by reference.

Where the toxins and IGF-1 receptor ligands are both proteins or peptides, the conjugates are preferably fusion proteins, expressed by recombinant DNA methods, of the toxins and the IGF-1 receptor ligands.

In particular embodiments of the toxin conjugates, the toxin is a calicheamicin or a derivative thereof (Merck Index $13^{th}$ edition, #1722). Specifically it may be calicheamicin $\gamma_1^I$ or a derivative thereof. Derivatization of the calicheamicins typically occurs on the trisulfide (Hamann, P. R. et al., 2005, Bioconjugate Chem. 16:346-353; Hinman, L. M. et al., pp. 87-106 in *Enediyne Antibiotics as Antitumor Agents*, D. B. Borders, T. W. Doyle, eds., Marcel Dekker Inc. New York, 1995). The calicheamicins are sometimes considered considered to be conventional anti-cancer chemotherapy agents in contradistinction to toxins. But they are treated as “toxins” herein because when administered systemically without conjugation to a targeting agent, at or below the doses that in the short term are most effective against tumors in an animal model, they exhibit almost 100% delayed lethality to the animals (Dun, F. E. et al. pp. 127-136 in *Enediyne Antibiotics as Antitumor Agents*, D. B. Borders, T. W. Doyle, eds., Marcel Dekker Inc. New York, 1995).

Preferably, an IGF-1 receptor ligand that is a protein (e.g., SEQ ID NO:1 or SEQ ID NO:2) is conjugated through one or more of its lysine residues to N-acetyl-calicheamicin $\gamma_1^I$. N-acetyl-calicheamicin $\gamma_1^I$ can be made by acetylating calicheamicin $\gamma_1^I$ in methanol in an excess of acetic anhydride. NAc-gamma calicheamicin dimethyl acid O-succinimidyl ester (compound 6 in Hamann, P. R. et al., 2005, *Bioconjugate Chem.* 16:346-353) is prepared as described in Hamann, P. R. et al., 2002, *Bioconjugate Chem.* 13:40-46. This activated succinimidyl ester reacts with amine groups on proteins to form an amide bond conjugate between the IGF-1 receptor ligand and N-acetyl-calicheamicin $\gamma_1^I$.

One embodiment of the invention is a method of treating cancer in a mammal involving administering to the mammal a therapeutically effective amount of an IGF-1 receptor ligand carrying a therapeutic radionuclide. In particular embodiments, the cancer is non-small cell lung cancer, prostate cancer, colorectal cancer, breast cancer, pancreatic cancer, Hodgkin's lymphoma, non-Hodgkin's lymphoma, leukemia, liver cancer, stomach cancer, ovarian cancer, uterine cancer, testicular cancer, brain cancer, or melanoma.

One embodiment of the invention is a method of treating cancer in a mammal involving administering to the mammal a therapeutically effective amount of a therapeutic agent containing an insulin-like growth factor-1 (IGF-1) receptor ligand linked to a toxin. In particular embodiments, the cancer is non-small cell lung cancer, prostate cancer, colorectal cancer, breast cancer, pancreatic cancer, Hodgkin's lymphoma, non-Hodgkin's lymphoma, leukemia, liver cancer, stomach cancer, ovarian cancer, uterine cancer, testicular cancer, brain cancer, or melanoma.

One embodiment of the invention is a method of inhibiting growth of cancer cells involving contacting the cancer cells with an IGF-1 receptor ligand carrying a therapeutic radionuclide. The contacting can be in vivo or in vitro. In particular embodiments, the IGF-1 receptor ligand carrying the therapeutic radionuclide kills the cancer cells.

Another embodiment of the invention is a method of inhibiting growth of cancer cells involving contacting the cancer cells with a therapeutic agent containing an IGF-1 receptor ligand linked to a toxin. The contacting can be in vitro or in vivo. In particular embodiments, the cancer cells are killed.

Another embodiment of the invention is a method of screening a compound for anti-cancer activity involving contacting cancer cells with a compound comprising an IGF-1 receptor ligand carrying a therapeutic radionuclide. The method involves monitoring the growth or killing of the cancer cells. The contacting can be in vitro or in vivo.

Another embodiment of the invention involves screening a compound for anti-cancer activity involving contacting cancer cells with a compound comprising an IGF-1 receptor ligand linked to a toxin. The method involves monitoring the growth or killing of the cancer cells. The contacting can be in vitro or in vivo.

The invention will now be illustrated by the following non-limiting examples.

Example 1

Treatment of a Mouse Breast Cancer Model with $^{131}$I-IGF-1 and $^{90}$Y-IGF-1

Materials and Methods

IGF is radioiodinated with 1-131 (Amersham Biosciences) by use of the IODO-GEN method (1,3,4,6-tetrachloro-3α, 6α-diphenylglycoluril; Pierce Biotechnology, Inc). Briefly, IGF-1 is incubated at room temperature in 85 μl PBS (0.1 M, pH 7.4) in a glass vial coated with 50-100 μg of IODO-GEN. After 10 min, the reaction is stopped by the addition of 100 μl of a saturated tyrosine solution. The reaction mixture then is separated on a PD-10 column (Amersham Biosciences), eluting with PBS and 0.5% bovine serum albumin. The specific activity is approximately 80 kBq/μg (Koppe, M. J. et al. 2004. *J. Nucl. Med.* 45:1224-1232).

To label with Y-90, IGF-1 is conjugated with isothiocyanato-benzyl-diethylenetriaminepentaacetic acid (ITC-DTPA, Macrocyclics, Inc.). ITC-DTPA is conjugated to IGF-1 in $NaHCO_3$ buffer (0.1 M, pH 8.2) by use of a 100-fold molar excess of ITC-DTPA as described by Ruegg et al. (Ruegg, C. L. et al., 1990, *Cancer Res.* 50:4221-26) for 1 hour at room temperature. The DTPA-IGF-1 conjugate is purified by dialysis against ammonium acetate buffer (0.1M, pH 5.0). The number of DTPA ligands per IGF-1 molecule can be determined by the method of Hnatowich, D. J. et al. 1983, *J. Immunol. Methods* 65:147-157. Up to three ligands may be conjugated per IGF-1. The purified DTPA-IGF-1 conjugate (0.8 mg/ml) is incubated with Y-90 (Perkin-Elmer Corp.) in ammonium acetate buffer (0.1 M, pH 5.4) at room temperature for 20 minutes. The specific activity is approximately 370 kBq/μg (Koppe, M. J. et al. 2004. *J. Nucl. Med.* 45:1224-1232).

The radiolabelled preparations are purified by gel filtration on a PD-10 column (Amersham), eluting with PBS with 0.5% bovine serum albumin. The amount of free radioisotope is determined by thin-layer chromatography with silica gel strips and citrate buffer (0.1 M, pH 6.0) as the mobile phase. Less than 5% of the label should be unconjugated to IGF-1.

The maximal tolerated dose of unlabelled IGF-1, $^{131}$I-IGF-1, and $^{90}$Y-IGF-1 is determined in six-week old female nude mice (nu/nu, Sprague Dawley, Madison, Wis.).

MCF-7 is a human breast cancer cell line that is responsive to IGF-1 (Dupont, J., et al., 2003, *J. Biol. Chem.* 278:37256). MCF-7 cells are cultured in F12/DME medium supplemented with 5% fetal calf serum (FCS) and 10 μg/ml insulin in 95% air, 5% $CO_2$ at 37° C. (Karey, K. P. et al., 1988, *Cancer Res.* 48:4083-4092.) Cells are transferred every 4-6 days and seeded at $1.75\times10^6$ cells/plate in 20 ml medium in a 10 cm dish.

MCF-7 cells are cultured as described above. Six-week-old female nude mice (nu/nu, Sprague Dawley, Madison, Wis.) are injected subcutaneously in the back with $5\times10^6$ MCF-7 cells in 0.05 ml serum-free medium. Estrogen production in the mice is inadequate to support growth of MCF-7, so the mice are given injections of beta-estradiol dissolved in sesame oil (0.1 mg/0.05 ml oil s.c.) beginning one day before injection of the cancer cells and weekly thereafter. Tumors are allowed to grow until a diameter of 5 mm. (Hardman, W. E., et al., 1999, *Anticancer Res.* 19:2269.)

When the tumors reach 5 mm, IGF-1, $^{131}$I-IGF-1, or $^{90}$Y-IGF-1 is injected at half its maximal tolerated dose in 5 mice each. Five control mice receive no agent.

Tumor size is monitored every 3 days.

Results:

It is determined that mice harboring MCF-7 tumors and receiving $^{131}$I-IGF-1 or $^{90}$Y-IGF-1 survive longer and have slower tumor growth than control mice receiving no treatment or receiving unlabelled IGF-1.

Example 2

Treatment of a Mouse Breast Cancer Model with IGF-1-dgRicin A Conjugate

Materials and Methods

Ricin A chain is prepared as described in Gregg, E. O. et al. (1987, *J. Immunol.* 138:4502-08). Ricin A chain is deglycosylated as described in Blakey, D. C. et al. (1987, *Cancer Res.* 47:947-952).

The conjugation procedure is generally as described in Thorpe, P. E. et al. (1982, *Immunol. Rev.* 62:119-158) and Huang, X. et al. (2004, *Prostate* 61:1-11). To a solution of IGF-1 (1 ml, 10 mg/ml) in 50 mM borate buffer (pH 9.0) was added 1.2 mg 4-succinimidyloxycarbonyl-methyl-α-[2-pyridyldithio]toluene (SMPT, Pierce Biotechnology) dissolved in 10 μl dimethylformamide. That is approximately a 3:1 molar ratio of SMPT to IGF-1. After 30 minutes stifling at room temperature, the reaction mixture is passed through a Sephadex G-25 column equilibrated with 0.1 M sodium acetate, 0.1 M NaCl, pH 4.5. The derivatized protein is eluted with the same buffer. Deglycosylated ricin A chain is derivatized with SMPT by the same procedure at a ratio of 2.6 SMPT per ricin A chain molecule. The derivatized deglycosylated ricin A is separated from reagents by passing the solution through a SEPHADEX G-25 column equilibrated with 0.1 M sodium acetate, 0.1 M NaCl, pH 4.5.

The derivatized IGF-1 is concentrated to 2.5 ml, and 10 mg of dithiothreitol is added. After stirring for 30 minutes at room temperature, the solution is passed through a SEPHADEX G-25 column equilibrated with nitrogen-flushed PBS. The eluted IGF-1 is run directly into a solution of the derivatized deglycosylated ricin A to react in a mixture with a 1:1.5 ratio of IGF-1 to deglycosylated ricin A (dgA). The reaction forms an IGF-1-dgA conjugate with 1 dgA per IGF-1.

Conjugates with 1 dgA per IGF-1 are purified by size-exclusion chromatography on SUPERDEX 200. The conjugate is characterized by SDS-PAGE to verify that the material consists of purified conjugate with 1 IGF-1 linked to 1 deglycosylated ricin A chain. The structure of the conjugate is shown below, where the linker is attached to lysine side chains or the N-terminal alpha-amino groups of the proteins.

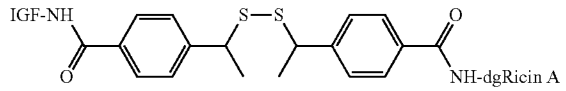

Mouse Treatment:

MCF-7 cells are cultured as described above. Six-week-old female nude mice (nu/nu, Sprague Dawley, Madison, Wis.) are injected subcutaneously in the back with $5\times10^6$ MCF-7 cells in 0.05 ml serum-free medium. Estrogen production in the mice is inadequate to support growth of MCF-7, so the mice are given injections of beta-estradiol dissolved in sesame oil (0.1 mg/0.05 ml oil s.c.) beginning one day before injection of the cancer cells and weekly thereafter. Tumors are allowed to grow until a diameter of 5 mm. (Hardman, W. E., et al., 1999, *Anticancer Res.* 19:2269.)

The maximal tolerated dose of the conjugate is determined by i.p. injection of a range of doses of the conjugate into mice. Then half the maximal tolerated dose of the conjugate is injected i.p. into 5 mice with 5 mm tumors. Five control mice with 5 mm tumors are untreated. Tumor size is monitored every 3 days thereafter.

Results:

It is determined that mice receiving the IGF-1-dgA conjugate survive longer and have slower tumor growth than control untreated mice.

Example 3

Treatment of a Mouse Breast Cancer Model with Diphtheria Toxin-IGF-1 Fusion Protein Materials and Methods:

A fusion protein containing at its N-terminus residues 1-389 of diphtheria toxin followed by a variant form (SEQ ID NO:10) of IGF-1 that does not bind to the soluble IGF binding proteins is synthesized. The diphtheria toxin-IGF-1 fusion protein (DPT-IGF-)1 is SEQ ID NO:12. It is expressed from a pET vector (G.E. Lifesciences) having the sequence of SEQ ID NO:14.

*E. coli* transformed with the SEQ ID NO:14 plasmid are grown in LB medium, with 50 μg/mlkanamycin at 37° C. At an O.D. 600 nm of approximately 0.4, 1 mM IPTG is added to stimulate expression of DPT-IGF-1 from the T7 promoter. After 4 hours, the cells are harvested. Cells are broken, inclusion bodies are collected and washed, and the fusion protein is purified from inclusion bodies as described in vanderSpek, J. C. et al., 2000, Meth. Enzymol. 327:239. The DPT-IGF-1 fusion protein is refolded by dilution to 0.1 mg/ml in 2 M urea, 50 mM Tris-HCl, 20 mM glycine, 1.5 mM EDTA, 0.4 mM dithiothreitol, pH 9.1 for 2 hours at room temperature. The refolded protein is concentrated by ultrafiltration.

The DPT-IGF-1 fusion protein is tested against MCF-7 breast cancer cells in mice by i.p. or i.v. injection as described in Examples 1 and 2.

Results:

It is determined that mice receiving the DPT-IGF-1 fusion protein survive longer and have slower tumor growth than control untreated mice.

Example 4

Treatment of a Mouse Breast Cancer Model with a *Clostridium perfringens* Enterotoxin-IGF-1 Fusion Protein Materials and Methods:

A fusion protein containing residues 45-223 of *Clostridium perfringens* enteroxin fused to a variant form (SEQ ID NO:10) of IGF-1 that does not bind to the soluble IGF-1 binding proteins is synthesized. This CPE-IGF-1 fusion protein is SEQ ID NO:11. In addition to the CPE moiety and the IGF-1 moiety, the fusion protein also contains at its N-terminus methionine followed by 6 His residues as a purification tag, followed by an enterokinase cleavage recognition sequence at residues 8-13. CPE residues 45-223 begin at residue 14 of the fusion protein. The variant IGF-1 moiety follows the CPE segment at the C terminal, beginning at residue 193 of the fusion protein. The fusion protein is encoded and expressed from a plasmid derived from a pET vector (GE Lifesciences). The plasmid sequence is SEQ ID NO:13.

*E. coli* transformed with the SEQ ID NO:13 plasmid are grown in LB medium, with 50 μg/mlkanamycin at 37° C. At an O.D. 600 nm of approximately 0.4, 1 mM IPTG is added to stimulate expression of DPT-IGF-1 from the T7 promoter. After 4 hours, the cells are harvested. Cells are broken as described in vanderSpek, J. C. et al., 2000, Meth. Enzymol. 327:239. The CPE-IGF-1 fusion protein is purified from the soluble fraction by passing the soluble fraction through a 10 ml packed column of HIS-SELECT nickel chelate affinity column (Sigma, St. Louis, Mo.). The CPE-IGF-1 fusion protein is eluted with 25 mM Tris, 250 mM imidazole, pH 8.0. The CPE-IGF-1 fusion protein is also purified from inclusion bodies as described in Example 3.

The CPE-IGF-1 fusion protein is tested against MCF-7 breast cancer cells in mice by i.v. or i.p. injection as described in Examples 1 and 2.

Results:

It is determined that mice receiving the DPT-IGF-1 fusion protein survive longer and have slower tumor growth than control untreated mice.

All cited patents, patent documents, and other references are incorporated by reference.

What is claimed is:

1. An anti-cancer therapeutic agent comprising:

an insulin-like growth factor-1 (IGF-1) receptor ligand carrying a therapeutic radionuclide; wherein the ligand is an IGF-1 receptor agonist;

wherein the ligand is a variant IGF-1 protein that has reduced binding affinity for soluble IGF-1 binding proteins; wherein the ligand comprises SEQ ID NO:10.

2. An anti-cancer therapeutic agent comprising:

an insulin-like growth factor-1 (IGF-1) receptor ligand carrying a therapeutic radionuclide; wherein the ligand is an IGF-1 receptor agonist;

wherein the ligand is a variant IGF-1 protein that has reduced binding affinity for soluble IGF-1 binding proteins; wherein the ligand comprises SEQ ID NO:9.

3. An anti-cancer therapeutic agent comprising:

an insulin-like growth factor-1 (IGF-1) receptor ligand carrying a therapeutic radionuclide; wherein the ligand is an IGF-1 receptor agonist;

wherein the ligand is a variant IGF-1 protein that has reduced binding affinity for soluble IGF-1 binding proteins; wherein the ligand comprises SEQ ID NO:2.

4. An anti-cancer therapeutic agent comprising:

an insulin-like growth factor-1 (IGF-1) receptor ligand carrying a therapeutic radionuclide; wherein the ligand is an IGF-1 receptor agonist;

wherein the ligand comprises IGF-2 (SEQ ID NO:8).

* * * * *